(12) United States Patent
Manneville

(10) Patent No.: US 7,578,171 B2
(45) Date of Patent: Aug. 25, 2009

(54) METHOD AND DEVICE FOR CHARACTERIZING A FLUID

(75) Inventor: Sébastien Manneville, Bordeaux (FR)

(73) Assignee: Centre National de la Recherche Scientifique - CNRS, Paris (FR)

( * ) Notice: Subject to any disclaimer, the term of this patent is extended or adjusted under 35 U.S.C. 154(b) by 0 days.

(21) Appl. No.: 10/576,135

(22) PCT Filed: Oct. 14, 2004

(86) PCT No.: PCT/FR2004/002624

§ 371 (c)(1),
(2), (4) Date: Mar. 6, 2007

(87) PCT Pub. No.: WO2005/043131

PCT Pub. Date: May 12, 2005

(65) Prior Publication Data

US 2008/0034844 A1    Feb. 14, 2008

(30) Foreign Application Priority Data

Oct. 21, 2003   (FR) .................................. 03 12279

(51) Int. Cl.
*G01N 11/10* (2006.01)
(52) U.S. Cl. ..................... 73/54.23; 73/54.28; 73/53.41; 73/54.24
(58) Field of Classification Search ................ 73/54.23, 73/54.41
See application file for complete search history.

(56) References Cited

U.S. PATENT DOCUMENTS

| 4,441,358 | A | 4/1984 | Osborne |
| 4,862,384 | A | 8/1989 | Bujard |
| 6,378,357 | B1 * | 4/2002 | Han et al. ................... 73/54.41 |
| 6,535,796 | B1 * | 3/2003 | Sierro et al. ................ 700/281 |

OTHER PUBLICATIONS

O'Donnell, Matthew. "Internal Displacement and Strain Imaging Using Ultrasonic Speckle Tracking". IEEE Transactions on Ultrasonics, Ferroelectrics, and Frequency Control. vol. 41, No. 3. May 1994. pp. 314-325.*
International Search Report dated Apr. 12, 2005 (in related PCT/FR2004/002624).

* cited by examiner

*Primary Examiner*—Hezron Williams
*Assistant Examiner*—Mark Shabman
(74) *Attorney, Agent, or Firm*—Miller, Matthias & Hull

(57) ABSTRACT

A method for the characterizing a fluid containing particles reflecting ultrasounds wherein a sample of fluid placed between two surfaces (5, 6) in a rheometer (1) undergoes stress in order to measure the rheological characteristics of the sample (8) during relative movement of the two surfaces (5,6) in relation to each other. Local ultrasound data relating to the sample (8) deformation is collected by ultrasonic-wave-measuring means (2,3,4). The invention also relates to a device for carrying out said method.

9 Claims, 4 Drawing Sheets

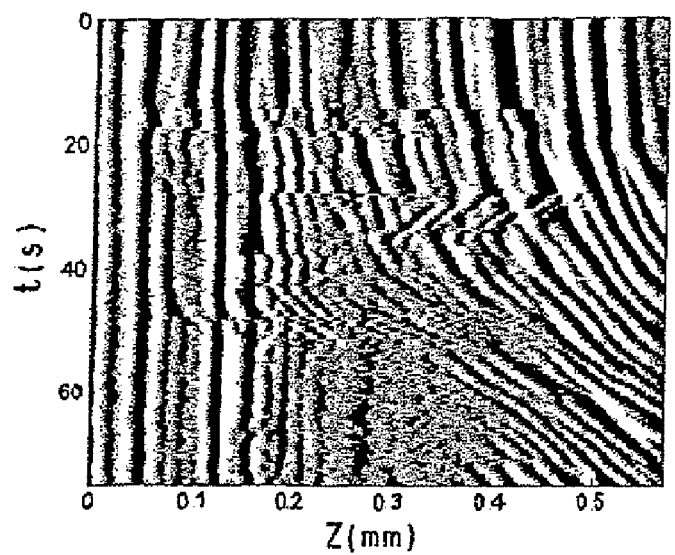
FIG. 7
FIG. 8.
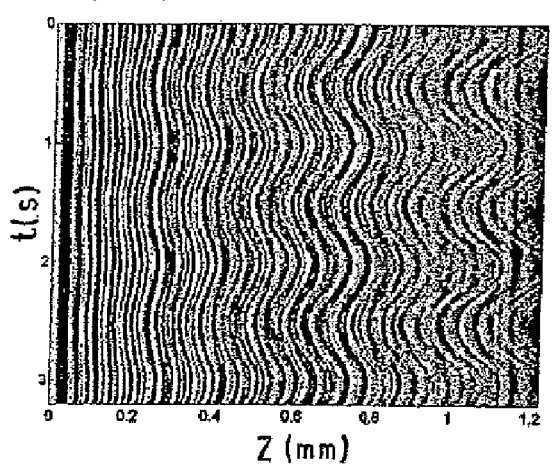
FIG. 9.
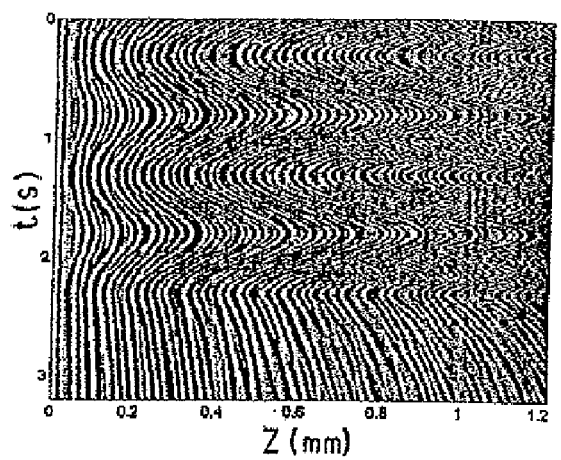
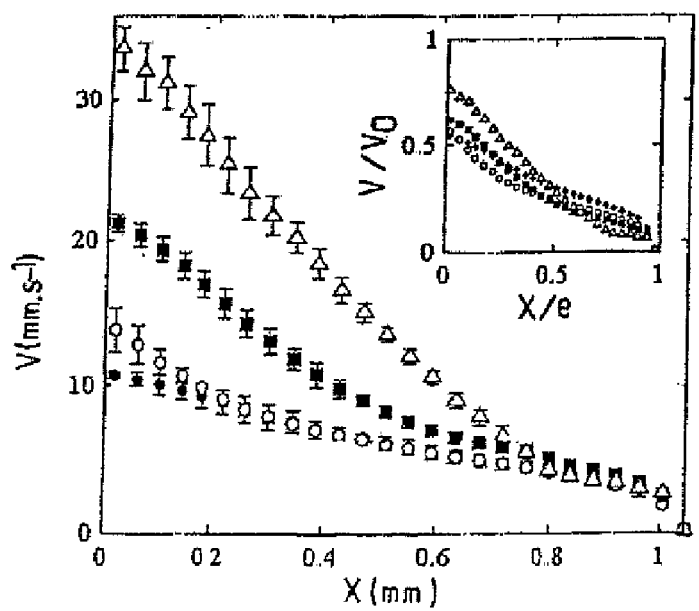
FIG. 10.

METHOD AND DEVICE FOR CHARACTERIZING A FLUID

CROSS-REFERENCE TO RELATED APPLICATION

This is the U.S. National Phase of International Application No. PCT/FR2004/02624 filed 14 Oct. 2004, the entire disclosure of which is incorporated herein by reference.

FIELD OF THE INVENTION

The present invention relates to methods and devices for characterizing a fluid under stress.

More particularly, the invention relates to a method and to a device for characterizing a fluid containing particles that reflect ultrasound, whether this occurs naturally or not. In the latter case, acoustic contrast agents may be employed. In this method, a specimen of the fluid placed between two surfaces is stressed in a rheometer for measuring the Theological characteristics of the specimen when the two surfaces undergo relative movement one with respect to the other.

BACKGROUND OF THE INVENTION

In the conventional rheology field, a rheometer is used to measure the deformation and flow behavior of a fluid when a stress is imposed thereon. The rheometer measures global Theological characteristics of the specimen of the fluid subjected to a stress set by the rheometer, the global rheological characteristics corresponding to data averaged over the volume of the specimen. These global rheological characteristics are relevant for fluids that undergo homogeneous deformations throughout the stressed specimen. The rheometer therefore proves to be an effective tool for studying fluids under what is called homogeneous flow, that is to say fluids whose rheological behavior is identical throughout the specimen.

However, it proves to be an incomplete tool for characterizing fluids whose rheological behavior is more complex, namely stressed fluids undergoing inhomogeneous local deformations, such as slip at the walls, local fractures, shear bands, etc.

Now, these complex fluids play a very important role in many industrial fields, such as in the food, chemical and cosmetics industries. Their study is therefore of great industrial importance.

OBJECTS OF THE INVENTION

The objective of the present invention is in particular to alleviate this drawback of conventional rheology.

For this purpose, a method according to the invention, of the kind in question, is essentially characterized in that local ultrasonic data relating to the deformation of the specimen are furthermore collected by ultrasonic wave measurement means.

Thanks to this arrangement, the movement of the fluid specimen can be measured locally.

This invention, which combines global and local rheological measurements, provides a complete, spatial and temporal, description of a fluid under stress.

This nonintrusive method allows a local rheological study of fluids that scatter ultrasonic waves, comprising fluids that scatter ultrasonic waves naturally and fluids that do not scatter ultrasonic waves naturally but acoustic contrast agents are added to them, this addition not disturbing the study. This local rheology method overcomes certain constraints associated with already existing optical methods, which are described in the documents "G. G. Fuller, J. M. Rallison, R. L. Schmidt and L. G. Leal, *J. Fluid Mech.*, 100, 555, (1980)" and "B. J. Ackerson, and N. A. Clark, *J. Physique*, 42, 929, (1981)", which cannot be applied to opaque specimens or specimens that scatter light too strongly. Thanks to this method, the range of fluids studied in local rheology is extended.

SUMMARY OF THE INVENTION

In preferred ways of implementing the method according to the invention, one or more of the following arrangements may optionally also be used:

the local ultrasonic data relating to the deformation of the specimen are collected by probing said specimen with ultrasonic waves with a frequency of above 20 MHz; the higher the frequency of the ultrasonic waves, the higher the spatial resolution of the local ultrasonic deformation data;

the operation of the rheometer delivers a temporal reference for the collection of the local ultrasonic data relating to the displacement of the specimen subjected to the stresses induced by the rheometer, which allows temporal correlation of global rheological data, averaged over the volume of the specimen, and of local ultrasonic data relating to the displacement of the specimen subjected to the stresses induced by the rheometer;

the local ultrasonic deformation data correspond to the displacement of a multitude of points along an axis Z, this multitude of points forming a substantially continuous field of observation, this method including an observation step during which:

several ultrasonic pulses are sent in succession into the specimen with a pulse repetition frequency of between 0 and 20 kHz;

echoes corresponding to each ultrasonic pulse reflected by the reflecting particles of the specimen are detected; and displacements in the specimen between two pulses for points in the field of observation are calculated locally using a cross-correlation technique on the ultrasonic local data;

a calibration step precedes the step of observing the displacement of the fluid specimen by means of ultrasonic waves, which calibration step is carried out along a Z axis and with a fluid specimen (a simple Newtonian fluid) for which the ultrasonic local data relating to deformation are known, and during which measurement correction factors are calculated by adjusting the known theoretical local specimen deformation data to the local deformation data measurements collected by means of the ultrasonic waves, these correction factors being due to problems of refraction at the surfaces of the specimen; the Z axis is determined experimentally according to the reflection index of the specimen so as to reduce the reflection of ultrasonic waves on the walls of the rheometer and to optimize a signal corresponding to the collected data;

said observation step carried out on a specimen under stress is followed by an image display step during which all the positions of a multitude of points on the Z axis are observed as a function of time, via the pressure amplitude on a pressure probe of the echoes corresponding to each ultrasonic pulse reflected by the reflecting particles of the specimen, it being possible for this amplitude to be chromatically coded;

said observation step is followed by a velocity calculation step on the basis of displacements of the points in the field of observation at a given instant, along the Z axis, then this calculation step is repeated several times and, after having averaged all the velocities obtained at each of the points in the field of observation, a velocity profile along the Z axis is determined;

several velocity profiles along the Z axis are determined in succession and at a frequency of between 0.1 Hz and 1 kHz. Given that a velocity profile can be produced in this way in 1 ms to 10 seconds, depending on the experimental conditions and the desired precision, the variation in the velocity profiles along the Z axis can therefore be studied with a high temporal resolution. Such a temporal resolution allows the dynamics of complex fluids to be monitored over time scales that are markedly shorter than other local measurement techniques such as light scattering or magnetic resonance imaging, which require acquisition times of the order of one minute;

the field of observation extends over at least a plane containing a first axis Z and a second axis Y that makes any angle with said first axis; and during said observation step, an array of several ultrasonic transducers placed along at least the Z axis is used in order to emit the ultrasonic pulses and to detect the echoes corresponding to each ultrasonic pulse reflected by the reflecting particles of the specimen (so as to supply an image of the displacements of the points in the field of observation at a given instant t.

Moreover, the subject of the invention is also a device, consisting of a rheometer for applying, between two surfaces in relative movement one with respect to the other, stresses to a specimen of the fluid lying between these two surfaces and for measuring rheological characteristics averaged over the volume of the specimen, characterized in that it further includes an ultrasonic device for measuring local deformations by ultrasonic wave measurement means, this ultrasonic device comprising:

an ultrasonic wave generator for sending such waves into the specimen, in a sequence of several firings; and an ultrasonic wave receiver for detecting the echoes reflected by the reflecting particles of the fluid that correspond to each ultrasonic wave firing, these echoes being used to locally monitor the deformation of the fluid as a function of time.

In preferred embodiments of the device according to the invention, the following arrangements may also be optionally employed:

the ultrasonic wave generator of the ultrasonic device is characterized in that it emits ultrasonic waves with a frequency of above 20 MHz; and the rheometer includes a Couette cell with a thickness of less than 4 mm.

Other features and advantages of the invention will become apparent over the course of the following description of several of its embodiments, given by way of nonlimiting example and with reference to the appended drawings.

BRIEF DESCRIPTION OF THE DRAWINGS

In the drawings:

FIG. 7 shows 150 successive echo signals detected during the movement of an organogel, according to the method of the invention;

FIG. 8 shows ultrasonic echo signals from concentrated emulsion subjected to a periodic stress oscillating at 1 Hz;

FIG. 9 shows ultrasonic echo signals from a dilute emulsion subjected to a periodic stress oscillating at 1 Hz;

FIG. 10 shows velocity profiles measured in an inhomogeneous fluid, exhibiting shear bands, according to the present invention;

FIG. 11b shows six successive velocity profiles recorded over a transient stress regime, shown in FIG. 11a.

DETAILED DESCRIPTION OF THE INVENTION

Figure 1:
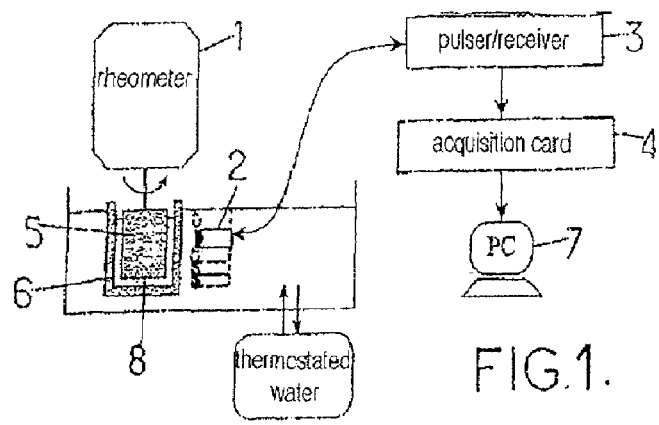
FIG. 1 is a schematic view of a device for characterizing a fluid according to one embodiment of the invention.

The device shown schematically in FIG. 1 comprises a rheometer 1, a transducer 2, a pulser/receiver 3 and an acquisition card 4 linked to a microcomputer 7. The rheometer 1 is an apparatus sold by TA Instruments under the reference AR 1000. It includes a Couette cell, consisting of two concentric Plexiglas® [PMMA] cylinders 5 and 6, the height of which is 30 mm and between which there is a fluid specimen 8. The gap between the two cylinders 5 and 6 varies between 0.5 mm and 1.1 mm depending on the specimen studied. The inner cylinder 5 forms a rotor, the rotation of which is controlled by the rheometer. It measures, in real time, the deformation, the stress and the shear rate applied to the fluid and records the global rheological characteristics of the specimen over the course of time, namely the shear modulus and the loss modulus in the small-deformation regime and the viscosity of the fluid in the large-deformation regime. It is important to note that the present invention can be adapted to other rheometer geometries, such as cone-plate or plate-plate.

Figure 2:
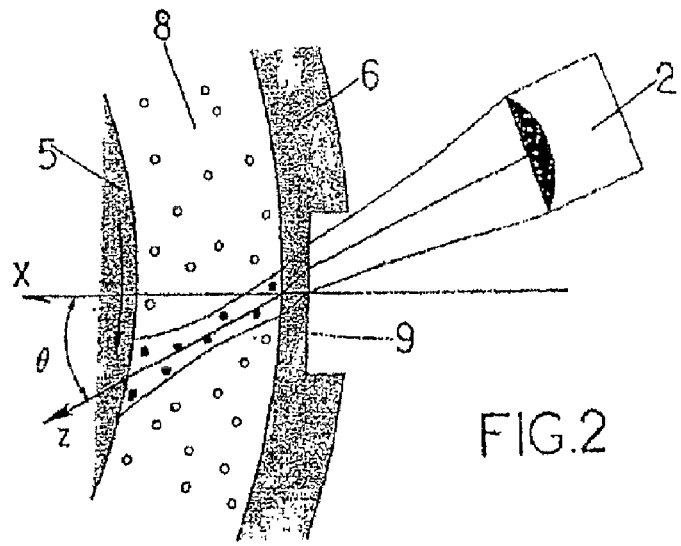
FIG. 2 is a schematic view from above of a relative arrangement of an ultrasonic device and a Couette-cell rheometer according to the embodiment of the invention shown in FIG. 1, in which the thickness of the outer wall of the Couette cell of the rheometer through which the ultrasonic waves pass has been locally reduced.

The transducer 2 is a broadband piezopolymer transducer sold by Panametrics under the reference PI 50-2. It is placed facing the stationary outer cylinder 6 (the stator), outside the Couette cell as indicated in FIG. 2. The transducer works both in emission mode and in receive mode, The assembly consisting of the transducer 2 and the Couette cell 5, 6 is placed in a rectangular tank (20 cm in length by 12 cm in width) which is fixed to the base of the rheometer 1 and in which distilled water circulates, the water temperature being controlled to ±0.1° C.

FIG. 2 shows a relative arrangement of the transducer 2 and the Couette cell, seen from above. The ultrasonic beam is focused in the fluid specimen 8 at mid-distance between the cylinders 5 and 6. The axis of the beam is identified by the direction Z, which makes an angle θ of incidence to the radial direction X of the rotor 5 and of the stator 6.

To minimize the thickness of the surface of the Couette cell through which the ultrasonic waves pass, a rectangular window 9 is made in the stator 6. The attenuation introduced by the travel through the stator is consequently reduced.

High-frequency ultrasonic pulses are emitted by the transducer 2 using the broadband pulser 3.

In one embodiment of the present invention, the frequency of these ultrasonic waves is centered at around 36 MHz and their emission corresponds to a firing with a typical duration of 0.1 microseconds. The spatial resolution obtained is around 40 microns. The spatial resolution of this method can be increased by using higher-frequency ultrasonic waves on condition that the ultrasonic absorption, which increases with frequency, does not excessively reduce the signal-to-noise ratio of the experiment.

These ultrasonic waves propagate in the water of the thermostated tank, passing through the stator 6 before penetrating the specimen 8.

After the emission or firing of a pulse, the pulser 3 receives and then filters and amplifies the echoes scattered by the specimen and picked up by the transducer 2. The output signal of the pulser 3 is then sent to the acquisition card 4 installed in the microcomputer 7, which stores the data on a hard disk.

Figure 3:
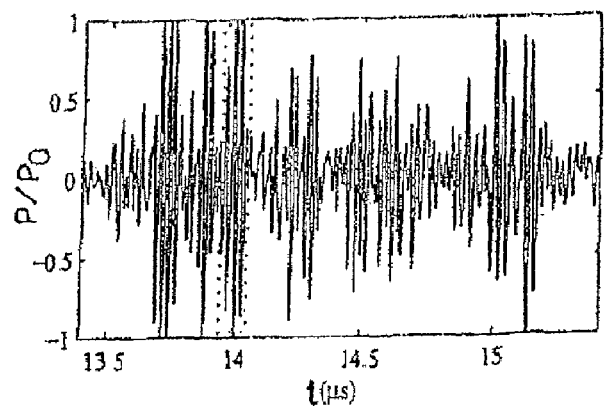
FIG. 3 is a signal of the echoes detected from a dilute suspension of polystyrene beads by the receiver of an ultrasonic device according to the embodiment of the invention shown in FIG. 1.

FIG. 3 shows an example of a recorded signal from a dilute suspension of polystyrene beads having a diameter of between 3 and 10 microns. It represents a complex system of ultrasonic echoes resulting from interference between the waves scattered by the medium.

In simple scattering regime, when the scatters are small compared with the ultrasound wavelength and the mean free path of the ultrasonic waves is large compared with the size of the specimen, the arrival time t of an echo corresponds to the position z, indicated on the Z axis, of the beam, of the scatterers that give rise to this echo, through the single equation:

$$z = c_0 t/2$$

where $c_0$ is the speed of propagation of the ultrasound in the specimen and the ½ factor results from the round trip between the transducer and the scatter. This equation between the arrival time t of the echoes and the position of the scatters forms the basis of any echographic measurement and therefore the basis of the present invention.

The device and the basic principle of this invention will now be explained in one of the possible embodiments.

The following sections will describe in greater detail the processing of the data collected then the results already obtained, by applying one possible way of implementing the method and one possible embodiment of the device according to the present invention.

In the method according to the invention, the specimen 8 is subjected to stresses by means of the rheometer 1 and local ultrasonic data relating to deformation of the specimen 8 are collected by the assembly consisting of the transducer 2, the pulser-receiver 3 and the acquisition card 4 linked to the microcomputer 7.

Figure 4:
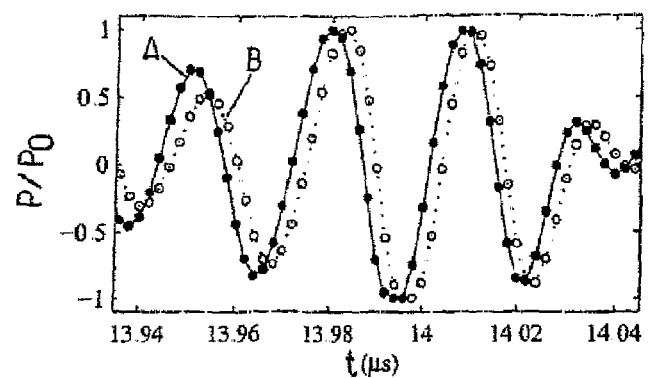
FIG. 4 is an enlarged portion of the signal shown in FIG. 3, formed from two echo signals corresponding to two successive pulses separated by 1 ms.

Thus, ultrasonic pulses are emitted and the echoes thereof are detected, FIG. 4 is an enlargement of one portion of FIG. 3. The signals A and B of FIG. 4 represent two successive echoes corresponding, respectively, to two successive ultrasonic pulses separated by 1 ms and detected by means of the transducer 2. Since the thickness of the specimen is less than 4 mm, it may be assumed that the movement of the scatters is "frozen" during the propagation of the ultrasonic waves. This is because the propagation of ultrasound through 1 mm of specimen takes about 2 microseconds, a sufficiently short time interval during which it may be considered that the relative positions of the scatters are unchanged.

FIG. 4 shows that, for a pulse repetition frequency of about 1 kHz, the time shift dt between two successive pulses can be easily measured, these being shown by the signal A and the signal B, respectively, in a portion of these signals.

Figure 5:
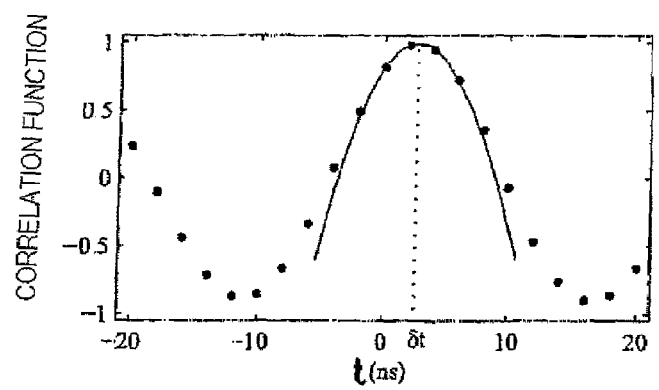
FIG. 5 shows a correlation function of the two signals of FIG. 4.

Mathematically, the data processing consists in cutting up two successive echo signals into narrow time slices, each corresponding to a different position z along the axis of the ultrasonic beam. FIG. 4 shows one of these narrow time slices, the position of which is identified by a dotted rectangle on the complete signal shown in FIG. 3. For each time slice, the two successive signal fragments are intercorrelated and the time shift dt between these two signals is estimated by calculating the position of the maximum of the correlation function after a parabolic interpolation near this maximum, as shown in FIG. 5. Examples of such correlation calculations are given in the prior art, for example by O'Donnell et al. ("Internal displacement and strain imaging using speckle tracking", IEEE Transactions on Ultrasonic, Ferroelectrics, and Frequency Control, Vol. 41, No. 3, May 1994, pp. 314-325).

For a time slice located around t, the displacement $dz = c_0 dt/2$ of one point in the specimen to the corresponding position $z = c_0 t/2$ is then deduced therefrom. Thus, a local measurement of the displacement dz in the specimen as the function of z between the two pulses is obtained.

Complementarily through the operations described above, a velocity calculation step is carried out on the basis of the local measurements of the displacements of the points in the field of observation at a given instant, along the Z axis. This calculation step is repeated several times, and after having averaged all the velocities obtained at each of the points in the field of observation, a velocity profile along the Z axis is determined.

The velocity at any given point is calculated in three steps. The first step corresponds to the calculation of the displacement of the points in the field of observation, as explained above, from which dz is obtained.

The second step consists in dividing dz by the time T separating two successive pulses, i.e. $v_z(z) = dz/T$. The ultrasonic pulse repetition frequency corresponds to 1/T. Finally, if it is assumed that the velocity field is purely orthoradial, it is easy to pass from the velocity $v_z(z)$ projected along the Z axis to the orthoradial velocity v(x) knowing the angle θ between the ultrasonic axis Z and the direction X.

In theory, two successive pulses are sufficient to determine the displacement of the specimen as a function of z. In practice, the ultrasonic echo signal is never perfectly homogeneous throughout the specimen and it is necessary to average the results obtained over 20 to 1000 ultrasonic wave firings in order to obtain a reliable velocity measurement for a given position. Thus, with a firing frequency of the order of kHz, a velocity profile is obtained in 0.02 to 2 seconds, whereas velocity profiles obtained by an optical method and an optical device, as mentioned above, take of the order of a minute. More generally, depending on the experimental conditions and the desired precision, a velocity profile may be obtained in 1 millisecond to 10 seconds.

To calibrate the device, a calibration step is carried out using a specimen consisting of a homogeneous fluid.

Figure 6:
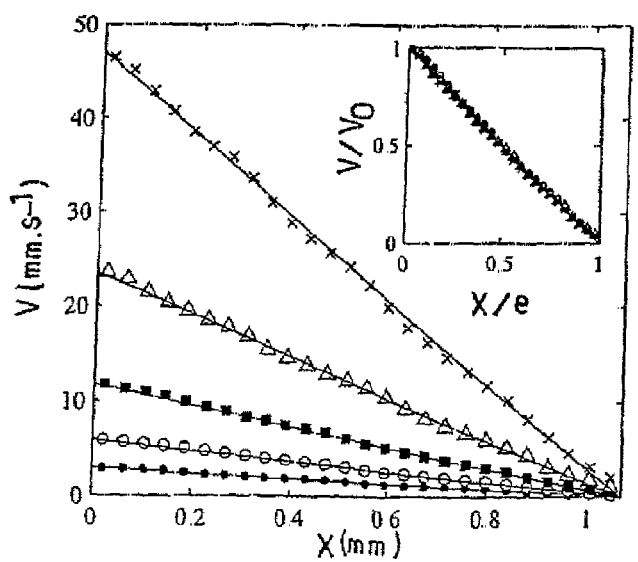
FIG. 6 shows velocity profiles measured in a homogeneous fluid corresponding to a Newtonian suspension of polystyrene beads, according to the present invention.

FIG. 6 shows velocity profiles of a homogeneous fluid, recorded for various shear rates imposed by the rheometer 1. The velocity profiles decrease linearly from the rotor 5 (at x=0) to the stator 6 (at x=1.1 mm) where the velocity is zero, since the fluid studied is homogeneous (a Newtonian fluid). These measurements allow the device to be calibrated in correlation with the geometrical parameters associated with the relative arrangement of the ultrasonic beam and the Couette cell, namely the position of the transducer 2 relative to the rotor 5 and to the stator 6 and the ultrasound angle of incidence θ.

This calibration makes it possible to detect:
the angle θ corresponding to the ultrasound angle of incidence;
an angular correction factor; and
a distance correction factor.

After calibration, the collection of the local ultrasonic deformation data for any specimen is carried out.

The collection of the local ultrasonic deformation data of this specimen under stress is followed by an image display step during which the positions of a multitude of points along the Z axis are observed as a function of time, the amplitude of the pressure detected by the transducer 2 for the echoes corresponding to each ultrasonic pulse reflected by the reflecting particles of the specimen, which may be chromatically coded, as shown in FIG. 7.

FIG. 7 shows 150 successive echo signals recorded during the movement of a toluene-based organogel in a rheometer, the thickness between the two cylinders 5 and 6 of which is 0.5 mm. The amplitude of the echo signals, which is gray-scale-coded, is shown as a function of the depth of penetration of the ultrasound in the specimen 8. The black lines correspond to the position of the reflecting particles constituting the organogel. In this case, the particles providing the gel with cohesion are in the form of rods about 10 microns in diameter by 100 microns in length, and they cause sufficient scattering of the ultrasound naturally. The axis of the abscissae z corresponds to the ultrasound propagation axis Z. The axis of the ordinates t indicates the time at which the ultrasonic pulse takes place. It may easily be seen that the movement starts at t=15 s. The stationary echoes close to the stator—the stationary surface of the rheometer—indicates the presence of a congealed zone, whereas complex spatio-temporal phenomena (an array of nonsteady-state fractures) seems to occur in the rest of the cell for t>15 s.

FIG. 8 and FIG. 9 show ultrasonic echo signals recorded during the movement of emulsions in a rheometer 1, in which the thickness between the two cylinders 5 and 6 is 1.1 mm. The axis of the abscissae z corresponds to the ultrasonic wave propagation axis. The axis of the ordinates indicates the time at which the ultrasonic pulses take place. In the case of the emulsions, the presence of small droplets of oil having acoustic properties different from the surrounding fluid also result in an ultrasonic echo signal.

FIG. 8 shows the results obtained for a concentrated emulsion, for which the movement of the echo signal is periodic, as in the case of an elastic solid, whatever the depth z.

FIG. 9 shows the results obtained for a dilute emulsion, which continues to flow after the oscillations cease (for t>2 s).

The acquisition and the display over the course of time of the successive echo signals makes it possible to visualize the Theological phenomena occurring in the specimen confined within a thickness substantially equal to 1 millimeter.

As a complement to the images obtained as indicated above, it is possible, by using the device and the method according to the invention, to determine velocity profiles in the manner already explained above. Thus, FIG. 10 shows velocity profiles obtained with the device and the method according to the invention in a complex fluid, namely a lyotropic lamella phase (a mixture of 20 g/l salt water, 78 wt % octanol and 6.5 wt % SDS (a surfactant)) to which 1 wt % of polystyrene beads was added. This type of experiment makes it possible in particular to study the phenomenon of wall slip. Wall slip is a recurrent problem in rheology and in industry, The flow is inhomogeneous with a highly sheared region close to the rotor, which progressively invades the entire cell when the speed $v_0$ of the rotor is increased. The insert in FIG. 10 shows the data normalized by the rotor speed $v_0$ and by the thickness e of the cell. Within the temperature/shear range studied, the velocity profiles v exhibit substantial wall slip (about 20 to 30% of the rotor speed $v_0$), The present invention therefore allows a direct measurement of the slip in complex fluids.

Figure 11A:
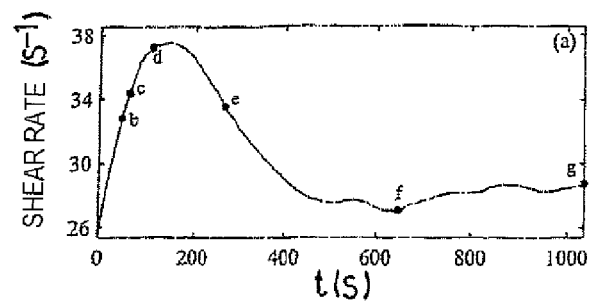
FIG. 11a shows the global shear rate recorded by the rheometer over the course of time.
Figure 11B:
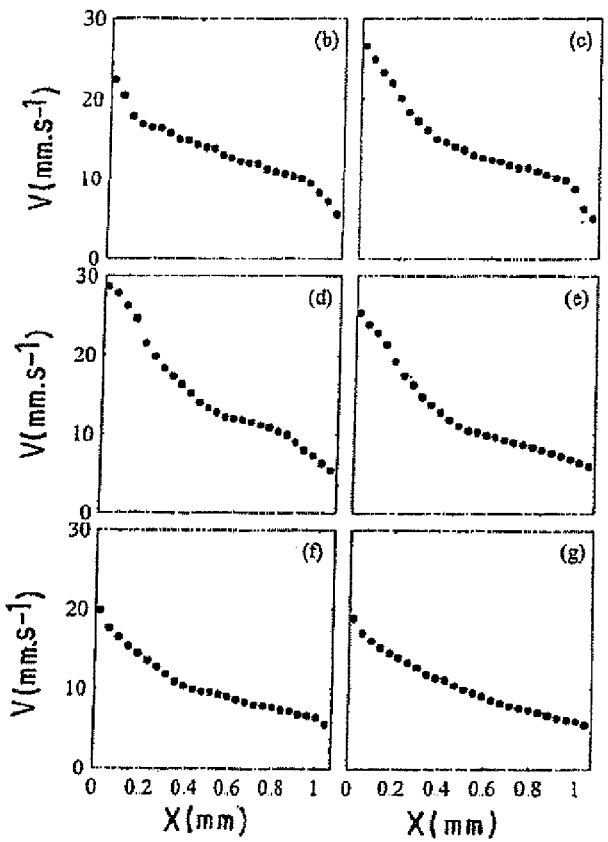

FIGS. 11a and 11b illustrate the capacity of the device described above to measure, simultaneously and with the same temporal reference, rheological quantities and velocity profiles, since the operation of the rheometer delivers a temporal reference for the collection of the local ultrasonic data relating to the displacement of the specimen subjected to the stresses induced by the rheometer.

FIG. 11b shows six successive velocity profiles recorded during a transient regime in which the stress applied to the specimen is suddenly increased, the rheological signature of which is shown in FIG. 11a, namely the speed $v_0$ of the rotor measured over the course of time by the rheometer. The device and the method of the present invention makes it possible to demonstrate the existence of inhomogeneous flow with three different shear zones and strongly nonsteady-state slip during the transient regime. The various shear bands coexist and then disappear during the transient regime.

Such local measurements are impossible using a conventional rheometer.

For these measurements, each velocity profile is obtained in 1.6 s. More generally, a velocity profile may be obtained in between 1 millisecond and 10 seconds depending on the experimental conditions and the desired precision. The present invention therefore enables a dynamic fluid characterization study to be carried out with a high temporal resolution.

Figure 12:
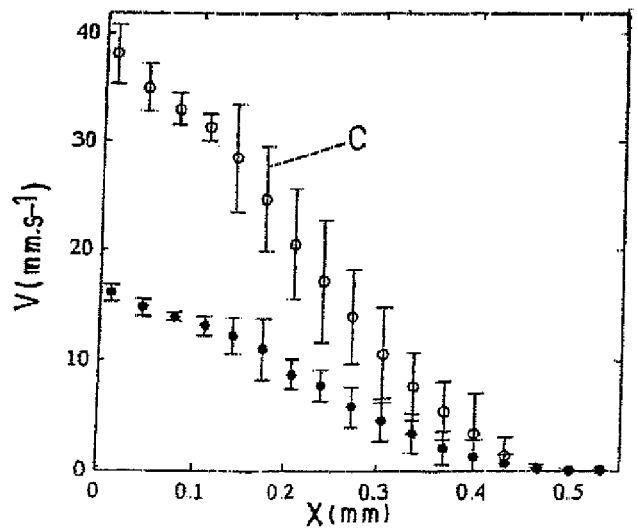
FIG. 12 shows velocity profiles in an organogel that are measured according to the present invention.

FIG. 12 shows measurements carried out on the toluene-based organogel already described in relation to FIG. 7. The velocity profiles in a Couette cell, in which the thickness between the cylinders 5 and 6 is 0.5 mm, show the coexistence of a nonflowing zone close to the stator 6 and a sheared zone in the rest of the cell.

The error bars C show the dispersion of the data due to the presence of fractures and highly nonsteady-state phenomena in the middle of the gel.

The invention claimed is:

1. A method for characterizing a fluid containing particles that reflect ultrasound waves, wherein a specimen of the fluid placed between two surfaces in a rheometer in order to measure rheological characteristics of the specimen is stressed when the two surfaces undergo relative movement one with respect to the other, wherein local ultrasonic data relating to the deformation of the specimen are simultaneously collected by ultrasonic wave measurement means and by ultrasonic data intercorrelation, wherein rheological characteristics of the fluid are determined, and wherein several velocity profiles along a Z axis are determined in succession and at a frequency of between 0.1 Hz and 1 kHz.

2. The method as claimed in claim 1, wherein the local ultrasonic data relating to the deformation of the specimen are collected by probing said specimen with ultrasonic waves with a frequency of above 20 MHz.

3. The method as claimed in claim 1, wherein the operation of the rheometer delivers a temporal reference for the collection of the local ultrasonic data relating to the displacement of the specimen subjected to the stresses induced by the rheometer.

4. The method as claimed in claim 1, wherein the local ultrasonic deformation data correspond to the displacement of a multitude of points along the axis Z, this multitude of points forming a substantially continuous field of observation, this method including an observation step during which:
- several ultrasonic pulses are sent in succession into the specimen with a pulse repetition frequency of between 0 and 20 kHz;
- echoes corresponding to each ultrasonic pulse reflected by the reflecting particles of the specimen are detected; and
- displacements in the specimen between two pulses for points in the field of observation are calculated locally using a cross-correlation technique on the ultrasonic local data.

5. The method as claimed in claim 4, wherein a calibration step precedes the step of observing the displacement of the fluid specimen by means of ultrasonic waves, which calibration step is carried out with a fluid specimen for which the theoretical local data relating to deformation are known and along an arbitrarily fixed firing axis Z, and during which measurement correction factors are calculated by adjusting the known theoretical local specimen deformation data to the local deformation data measurements collected by means of the ultrasonic waves.

6. The method as claimed in claim 4, wherein said observation step is followed by an image display step during which all the positions of a multitude of points on the Z axis are observed as a function of time, via the pressure amplitude on a transducer of the echoes corresponding to each ultrasonic pulse reflected by the reflecting particles of the specimen, it being possible for this amplitude to be chromatically coded.

7. The method as claimed in claim 4, wherein said observation step is followed by a velocity calculation step on the basis of displacements of the points in the field of observation at a given instant, along the Z axis, then this calculation is repeated several times and, after having averaged all the velocities obtained at each of the points in the field of observation, a velocity profile along the Z axis is determined.

8. The method as claimed in claim 4, wherein the field of observation extends over at least a plane containing a first axis Z and a second axis Y that makes any angle with said first axis.

9. The method as claimed in claim 4, wherein, during said observation step, an array of several ultrasonic transducers placed along at least the Z axis is used in order to emit the ultrasonic pulses and to detect the echoes corresponding to each ultrasonic pulse reflected by the reflecting particles of the specimen so as to supply an image of the displacements of the points in the field of observation at a given instant.

* * * * *

UNITED STATES PATENT AND TRADEMARK OFFICE
CERTIFICATE OF CORRECTION

PATENT NO.       : 7,578,171 B2                                              Page 1 of 1
APPLICATION NO.  : 10/576135
DATED            : August 25, 2009
INVENTOR(S)      : Manneville It is certified that error appears in the above-identified patent and that said Letters Patent is hereby corrected as shown below:

**Column 1, line 20, please replace "Theological" with --Rheological--
**Column 10, line 25, please insert --t-- at the end of "... at a given instant --t--."

Signed and Sealed this

Ninth Day of February, 2010

David J. Kappos
*Director of the United States Patent and Trademark Office*